US00PP25671P3

(12) United States Plant Patent
Kellerhals

(10) Patent No.: US PP25,671 P3
(45) Date of Patent: Jul. 7, 2015

(54) APPLE TREE NAMED 'LADINA'

(50) Latin Name: ***Malus domestica* Borkh**
Varietal Denomination: Ladina

(71) Applicant: Agroscope Changins-Wädenswil, Wädenswil (CH)

(72) Inventor: Markus Kellerhals, Wädenswil (CH)

(73) Assignee: Agroscope Changins-Wädenswil, Wädenswil (CH)

( * ) Notice: Subject to any disclaimer, the term of this patent is extended or adjusted under 35 U.S.C. 154(b) by 75 days.

(21) Appl. No.: 13/815,197

(22) Filed: Feb. 7, 2013

(65) Prior Publication Data

US 2014/0223621 P1 Aug. 7, 2014

(51) Int. Cl.
*A01H 5/00* (2006.01)

(52) U.S. Cl.
USPC ..... Plt./161
CPC ..... *A01H 5/00* (2013.01)

(58) Field of Classification Search
USPC ..... Plt./161
See application file for complete search history.

(56) References Cited

PUBLICATIONS

Pluto Plant Variety Database 20140812 search for plant Ladina. p. 1.*

* cited by examiner

*Primary Examiner* — Annette Para
(74) *Attorney, Agent, or Firm* — Michelle Bos

(57) ABSTRACT

'Ladina' is a new apple tree produced by a controlled cross of 'Topaz' and 'Fuji' and selected for its resistance to scab and low susceptibility to powdery mildew and fire blight. 'Ladina' apples are obloid in shape, with an attractive solid flush coloration and sweet juicy flesh.

4 Drawing Sheets

Latin name: *Malus domestica* Borkh.
Variety denomination: 'Ladina'.

BACKGROUND OF THE VARIETY

'Ladina' is a new and distinct variety of apple tree selected from seedlings produced as the result of a controlled cross made in 1999 at Wädenswil, Switzerland, of 'Topaz' (female parent, not patented) and 'Fuji' (male parent, not patented). The new variety was selected for further evaluation due to its resistance to scab (Vf) and its low susceptibility to powdery mildew and fire blight. The selection was asexually propagated by grafting in 2004 at Wädenswil, and was subsequently observed over successive asexually propagated generations. The tree and its fruit have been found to remain true to type and to retain the desirable characteristics for which the variety was selected.

BRIEF DESCRIPTION OF THE VARIETY

'Ladina' apple trees are resistant to scab and show low susceptibility to powdery mildew and fire blight. 'Ladina' apples are obloid in shape, with an attractive solid flush coloration and sweet juicy flesh. The fruit of 'Ladina' are distinguished from 'Topaz' by a larger area of overcolor, more solid flush, and deeper eye basin, and from 'Fuji' by a larger area of overcolor, deeper intensity of overcolor, more obloid shape, and higher acid content.

BRIEF DESCRIPTION OF THE PHOTOGRAPHS

Figure 1:
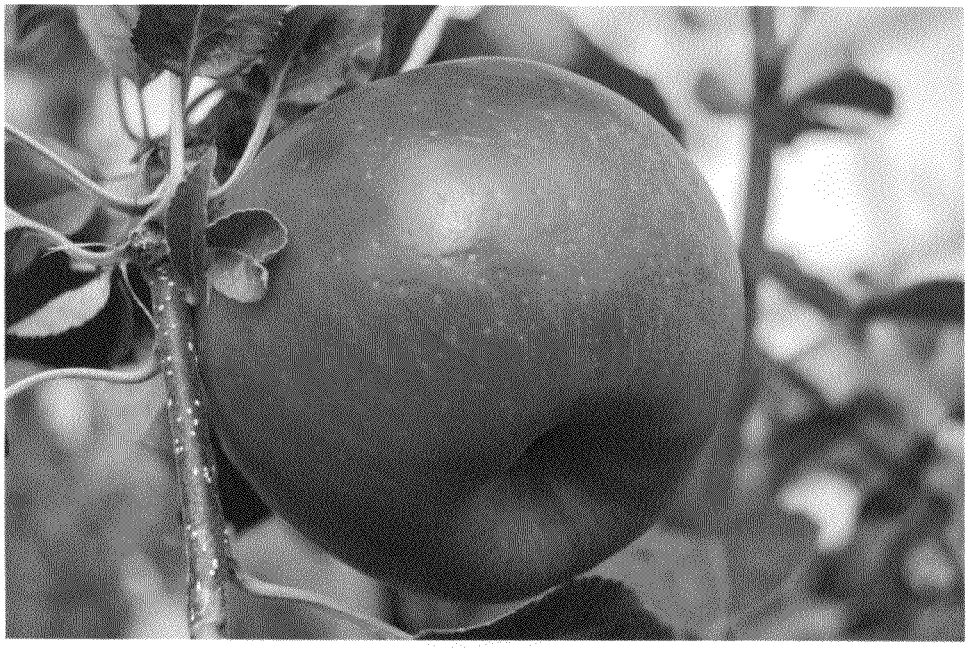
Figure 2:
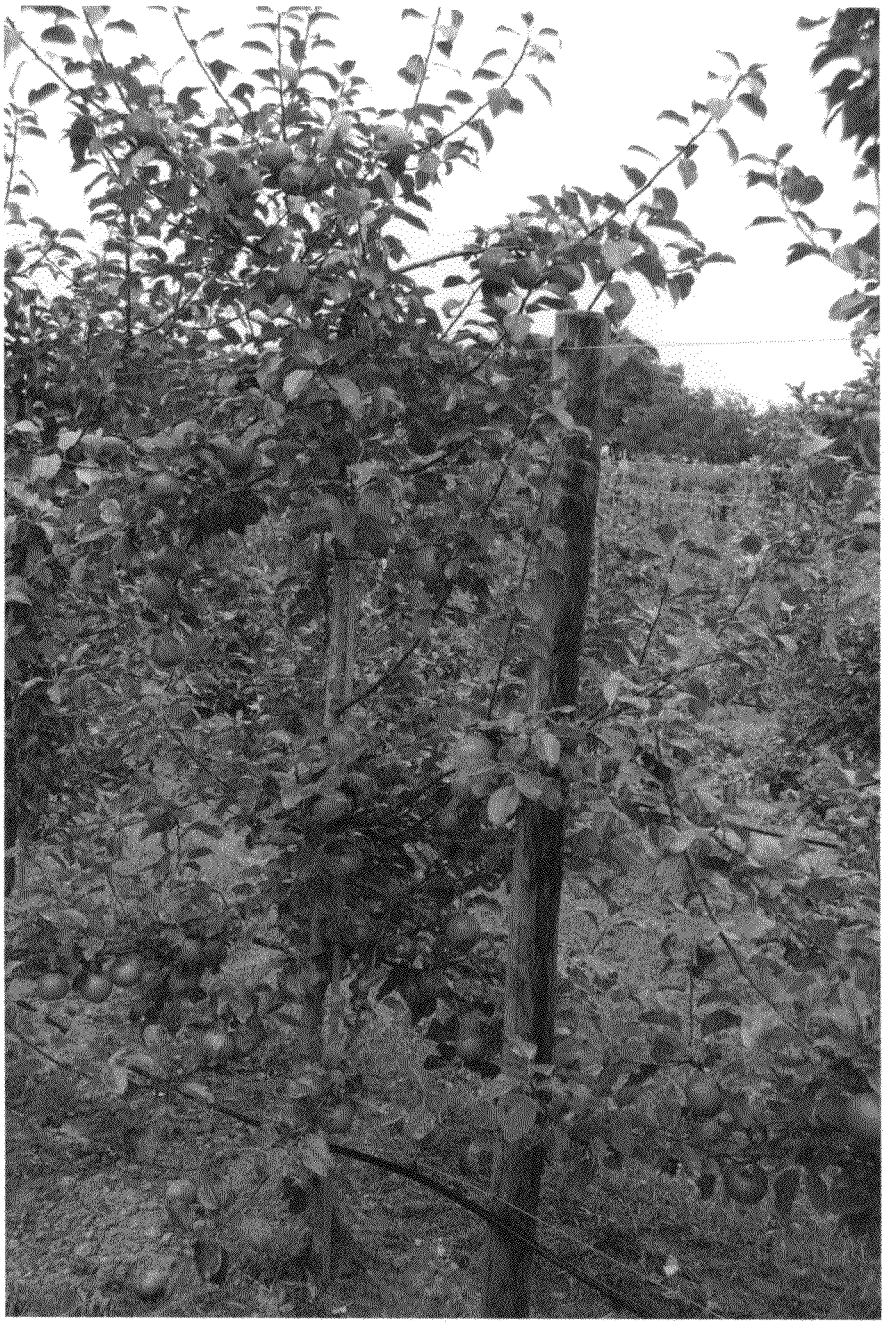
Figure 3:
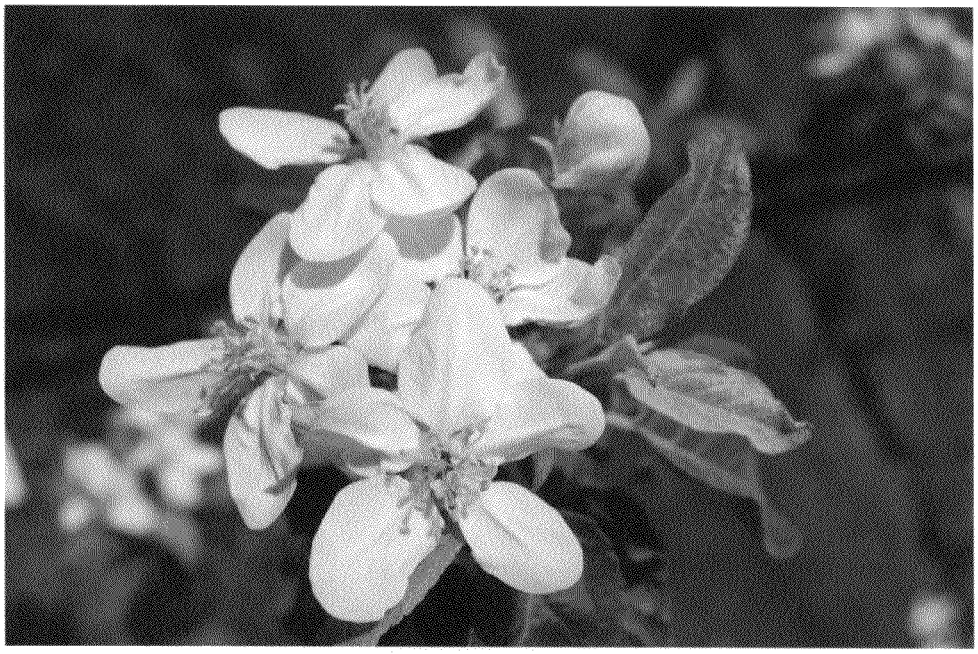
Figure 4:
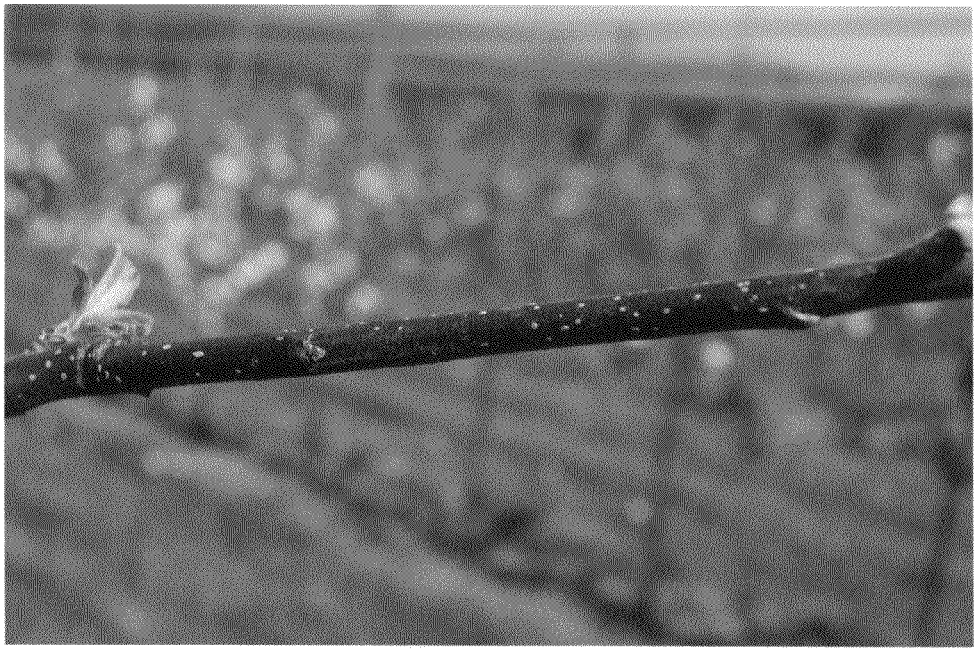

FIG. 1 shows a fruit of the new variety;
FIG. 2 shows a tree, fruit and leaves of the variety;
FIG. 3 shows a blossom of the new variety; and
FIG. 4 shows a one year old shoot of the variety.

DETAILED BOTANICAL DESCRIPTION OF THE VARIETY

The following detailed botanical description is based on observations made during the 2011 and 2012 growing seasons at Wädenswil, Switzerland (600 m above sea level) of trees planted in 2010 on 'M9 T337' rootstock (not patented) in high density plantings. All colors are described according to The Royal Horticultural Society Colour Chart ($5^{th}$ ed.). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium.
*Type*.—Ramified.
*Habit*.—Spreading.
*Height*.—2 m.
*Trunk diameter* (*at* 30 *cm above the graft*).—1.9 cm.
*Bark texture*.—Fine.
*Bark coloration*.—Grey-brown N199B.

Branch (fruiting branches located at about 1 m above the graft union):

*Length*.—54 cm.
*Diameter*.—1 cm.
*Crotch angle*.—90°.
*Bark color*.—Grey-brown N199B.
*Lenticel length*.—1.5 mm.

*Lenticel color*.—White 155D.
*Number of lenticels per cm²*.—5.
One year old shoot:
*Length*.—41 cm.
*Color*.—Greyed-orange 177A.
*Pubescence*.—Weak.
*Thickness*.—0.5 cm.
*Internode length*.—2.6 cm.
*Pubescence*.—Weak.
*Number of lenticels per cm²*.—8.
Flower buds:
*Quantity per spur*.—3.
*Shape*.—Conical.
*Length*.—11 mm.
*Diameter*.—8 mm.
*Color*.—Red-purple 65C.
Flowers:
*Diameter of fully open flower*.—43 mm.
*Relative position of petal margin*.—Free.
*Number per cluster*.—5.
*Date of first bloom*.—Intermediate to late (23 April in 2012).
*Date of full bloom*.—30 April in 2012.
*Pollination requirement*.—Pollinator required, e.g., 'Topaz'.
Petals:
*Number per flower*.—5.
*Shape*.—Oval.
*Length*.—20 mm.
*Width*.—12 mm.
*Apex*.—Round.
*Base*.—Pointed.
*Margin*.—Smooth.
*Color of upper surface*.—White N155B with pink vein 70D.
*Color of lower surface*.—Red-purple 62D.
Pistils:
*Size*.—12 mm.
*Color*.—Yellow-green 149C.
Stigma:
*Size*.—1 mm.
*Color*.—Yellow-green 150C.
Style:
*Size*.—10 mm.
*Color*.—Yellow-green 144C.
Ovary:
*Size*.—6 mm.
*Color*.—Green 141D.
Anthers:
*Quantity*.—16.
*Size*.—2 mm.
*Presence of pollen*.—Present.
*Color of pollen*.—Yellow 4B.
Pedicel:
*Length*.—22 mm.
*Diameter*.—1.4 mm.
*Color*.—Green 141D.
Sepals:
*Quantity*.—5.
*Coloration*.—Green 141D.
*Shape*.—Conical pointed.
*Margin*.—Smooth.
Leaves:
*Shape*.—Elliptic.
*Length*.—5 cm (without style).
*Width*.—3 cm.
*Length/width ratio*.—1.3.
*Blade margin*.—Serrulate.
*Apex*.—Round.
*Base shape*.—Pointed.
*Color of upper surface*.—Green N137B.
*Color of lower surface*.—Yellow-green 147B.
*Attitude in relation to shoot*.—Downwards.
Petiole:
*Length*.—2 cm.
*Diameter*.—1.2 mm.
*Coloration*.—Yellow-green 144B.
Fruit:
*Quantity per cluster*.—1 to 3.
*Diameter*.—76 mm.
*Weight*.—163 g.
*Ratio of height to width*.—Medium.
*General shape in profile*.—Globose, tending toward obloid.
*Position of maximum diameter*.—Toward petiole.
*Ribbing*.—Absent.
*Crowning at calyx end*.—Moderate.
*Size of eye*.—Small to medium.
*Aperture of eye*.—Closed.
*Length of sepal*.—Short.
*Bloom of skin*.—Absent or weak.
*Greasiness of skin*.—Absent.
*Amount of over color*.—Large.
*Over color of skin*.—Red 46A.
*Intensity of over color*.—Medium.
*Pattern of over color*.—Solid flush with weakly defined stripes.
*Amount of russet around stalk cavity*.—Absent or weak.
*Amount of russet on cheeks*.—Absent.
*Area of russet around eye basin*.—Absent.
*Length of stalk*.—26 mm.
*Thickness of stalk*.—2.2 mm.
*Depth of stalk cavity*.—Medium, 12 mm.
*Width of stalk cavity*.—Medium, 34 mm.
*Depth of eye basin*.—Medium, 9 mm.
*Width of eye basin*.—Medium, 30 mm.
*Firmness of flesh*.—Firm.
*Flesh texture*.—Fine.
*Aroma*.—Sweet.
*Juiciness*.—Very juicy.
*Brix*.—12.5°.
*Flesh color*.—Yellow 11C.
*Stem color*.—Yellow-green 152B.
Seeds:
*Quantity per fruit*.—9.
*Shape*.—Oval-oblong.
*Color*.—Greyed-orange 165B.
Harvest:
*Time of harvest*.—Mid-September, first pick about 10 to 14 days after Gala.
*Number of picks*.—2.
*Number of fruit produced per tree per harvest*.—30.
Disease resistance/susceptibility: Scab resistant (Vf), low susceptibility to powdery mildew and fire blight (greenhouse tested for shoot and blossom, and field test with artificial flower inoculation).
Market use: Table fruit.

I claim:
1. A new and distinct apple tree substantially as described and illustrated herein.

* * * * *